(12) United States Patent
Subrin

(10) Patent No.: US 9,132,617 B2
(45) Date of Patent: Sep. 15, 2015

(54) SCENT RELEASING ARTICLES AND METHODS FOR PREPARING THE SAME

(76) Inventor: Michelle Subrin, Carmel, IN (US)

( * ) Notice: Subject to any disclaimer, the term of this patent is extended or adjusted under 35 U.S.C. 154(b) by 825 days.

(21) Appl. No.: 13/292,042

(22) Filed: Nov. 8, 2011

(65) Prior Publication Data

US 2013/0112769 A1  May 9, 2013

(51) Int. Cl.
| | |
|---|---|
| A61L 9/04 | (2006.01) |
| B32B 38/04 | (2006.01) |
| B32B 37/04 | (2006.01) |
| A61L 9/12 | (2006.01) |
| A44C 15/00 | (2006.01) |

(52) U.S. Cl.
CPC ............... *B32B 37/04* (2013.01); *A61L 9/042* (2013.01); *A61L 9/12* (2013.01); *A44C 15/002* (2013.01); *B32B 2305/18* (2013.01); *B32B 2305/38* (2013.01); *B32B 2307/70* (2013.01); *Y10T 29/49826* (2015.01); *Y10T 156/1043* (2015.01); *Y10T 156/1054* (2015.01)

(58) Field of Classification Search
USPC .............. 264/319, 320, 324, 340; 239/36
IPC  B32B 37/04,2305/18, 2305/38, 2307/70; A61L 9/042, 9/12; Y10T 29/49826, 156/1054, 156/1043; A44C 15/002
See application file for complete search history.

(56) References Cited

U.S. PATENT DOCUMENTS

| | | | |
|---|---|---|---|
| 2,214,842 A * | 9/1940 | Sweet et al. ...................... 428/46 |
| 4,283,011 A * | 8/1981 | Spector ............................ 239/36 |
| 4,293,602 A | 10/1981 | Coffey et al. | |
| 4,465,232 A | 8/1984 | Field | |
| 4,744,514 A | 5/1988 | Gadoua | |
| 4,802,626 A | 2/1989 | Forbes et al. | |
| 4,854,501 A | 8/1989 | Ricci | |
| 4,880,690 A | 11/1989 | Szycher et al. | |
| 5,031,419 A | 7/1991 | Gelman | |
| 5,071,704 A | 12/1991 | Fischel-Ghodsian | |
| 5,087,273 A | 2/1992 | Ward | |
| 5,148,983 A | 9/1992 | Muniz | |
| 5,156,843 A | 10/1992 | Leong et al. | |
| 5,232,769 A | 8/1993 | Yamato et al. | |

(Continued)

FOREIGN PATENT DOCUMENTS

WO    2010111732    10/2010

OTHER PUBLICATIONS

International Search Report and Written Opinion, Jan. 25, 2013, pp. 1-6, International Searching Authority, Alexandria, VA.

*Primary Examiner* — Mathieu Vargot
(74) *Attorney, Agent, or Firm* — Krieg DeVault LLP

(57) ABSTRACT

Scent releasing articles and methods for producing the same are provided. In one embodiment, a method includes absorbing a first amount of fragrant oil with a polymer material and positioning the polymer material between opposing layers of mesh material each defining a plurality of interstitial openings to form a composite structure. The composite structure is then heated and pressed to fill at least a portion of the interstitial openings of the opposing layers of mesh material with a portion of the polymer material. In one form, the method further includes contacting the composite structure with a second amount of fragrant oil. In another embodiment, the polymer material is positioned between a mesh material defining a plurality of interstitial openings and an oil impermeable barrier material, which can optionally also include a mesh layer. Other embodiments include unique methods, systems, kits, assemblies, equipment, and/or apparatus which involve scent releasing articles.

13 Claims, 2 Drawing Sheets

(56) References Cited

U.S. PATENT DOCUMENTS

| | | |
|---|---|---|
| 5,391,420 A | 2/1995 | Bootman et al. |
| 5,422,078 A | 6/1995 | Colon |
| 5,455,043 A | 10/1995 | Fischel-Ghodsian |
| 5,529,243 A | 6/1996 | Hoyt et al. |
| 5,670,219 A | 9/1997 | Na |
| 5,678,251 A | 10/1997 | Getz |
| 5,707,696 A | 1/1998 | Boxler |
| 5,776,378 A | 7/1998 | Knight |
| 5,782,408 A | 7/1998 | Carter |
| 5,809,557 A | 9/1998 | Shemla et al. |
| 5,889,790 A | 3/1999 | Fukuda |
| 5,985,774 A | 11/1999 | Capel |
| 6,051,547 A | 4/2000 | Ornitz |
| 6,073,772 A | 6/2000 | Forbes et al. |
| 6,101,981 A | 8/2000 | Friend et al. |
| 6,173,675 B1 | 1/2001 | Licciardo |
| 6,207,274 B1 | 3/2001 | Ferenc et al. |
| 6,291,371 B1 | 9/2001 | Shefer et al. |
| 6,357,260 B1 | 3/2002 | Lutz |
| 6,430,764 B1 | 8/2002 | Peters |
| 6,517,759 B1 | 2/2003 | Ferenc et al. |
| 6,640,715 B1 | 11/2003 | Watson et al. |
| 6,703,011 B2 | 3/2004 | Shefer et al. |
| 7,045,204 B2 | 5/2006 | Enguchi |
| 7,073,729 B2 | 7/2006 | Putz |
| 7,185,613 B2 | 3/2007 | Arvanitis |
| 7,427,417 B2 | 9/2008 | Jendrucko et al. |
| 7,437,061 B2 | 10/2008 | Manne |
| 7,455,864 B2 | 11/2008 | Heuer et al. |
| 7,484,716 B2 | 2/2009 | Ford Morie et al. |
| D595,524 S | 7/2009 | Sammons |
| 7,594,344 B2 | 9/2009 | Mizrahi |
| 7,631,814 B2 | 12/2009 | Zarembinski |
| 7,754,198 B2 | 7/2010 | Whitehead et al. |
| 7,833,515 B2 | 11/2010 | Corzani et al. |
| 7,887,826 B2 | 2/2011 | Costa |
| 7,919,666 B2 | 4/2011 | Odorzynski |
| 2002/0139140 A1 | 10/2002 | Schaab |
| 2003/0199421 A1 | 10/2003 | Copfer |
| 2004/0121111 A1 | 6/2004 | Hurwitz |
| 2006/0219189 A1 | 10/2006 | Arvanitis |
| 2008/0105760 A1 | 5/2008 | Sheffield et al. |
| 2008/0295457 A1 | 12/2008 | Kaniecki et al. |
| 2010/0102142 A1 | 4/2010 | Tagliareni |
| 2010/0223953 A1* | 9/2010 | Juan .............................. 63/1.15 |

\* cited by examiner

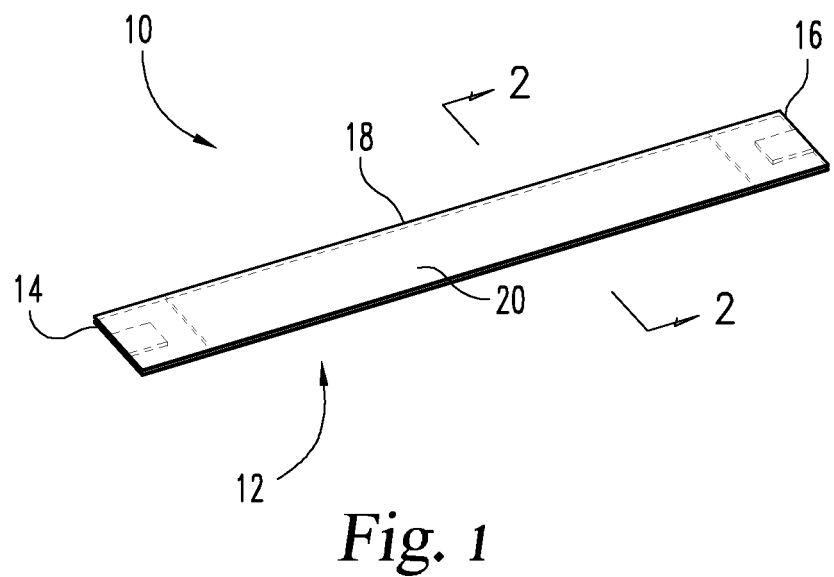
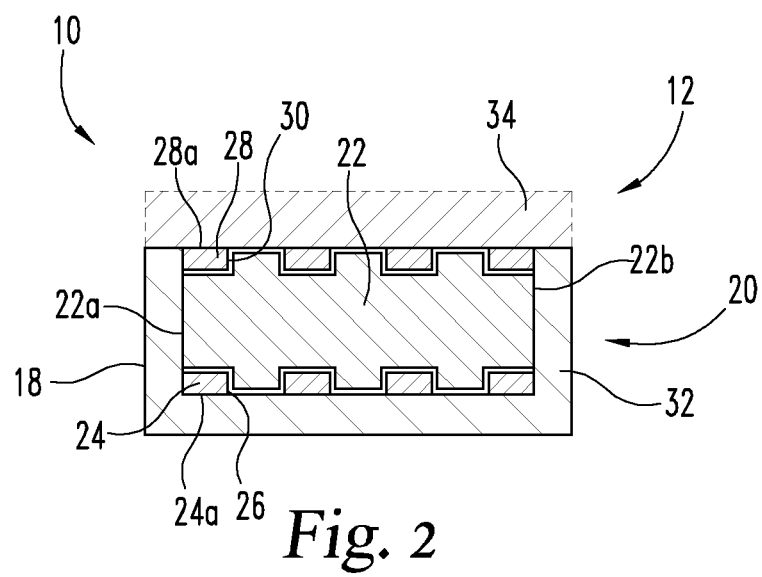

SCENT RELEASING ARTICLES AND METHODS FOR PREPARING THE SAME

The present application relates to scent releasing articles and methods for preparing the same, and more particularly, but not exclusively, to scent releasing articles including a polymer material that contains a fragrant material and is at least partially integrated into a mesh material.

Scent releasing articles can be advantageous for a variety of reasons. For example, a scent releasing article can be worn by a user in lieu of perfumes or colognes, which can be irritating to the user when placed in direct contact with his/her skin. However, the configurations of some current scent releasing articles can be limiting on the operability of the article to release a scent or aroma for a desired period of time. In addition, these configurations can also be limiting on the applications for which the scent releasing articles may be deployed. By way of non-limiting example, the ability to conveniently and portably receive the benefits of aroma therapy from essential oils is generally not facilitated by current scent releasing articles. Thus, there is a need for additional contributions in this area of technology.

One embodiment of the present application is directed to a method that includes absorbing a first amount of fragrant oil with a polymer material and positioning the polymer material between opposing layers of mesh material each including a plurality of interstitial openings to form a composite structure. The composite structure is then heated and pressed to fill at least a portion of the interstitial openings of the opposing layers of mesh material with a portion of the polymer material to produce a scent releasing article. In one form, the method further includes contacting the scent releasing article with a second amount of fragrant oil. In yet another form, it is also contemplated that the first amount of fragrant oil can be absorbed by the polymer material after the composite structure has been heated and pressed, and that the scent releasing article may then be optionally contacted with a second amount of fragrant oil. In another embodiment, the polymer material is positioned between a mesh material defining a plurality of interstitial openings and an oil impermeable barrier material, which can optionally also include a mesh layer.

Another embodiment of the present application is a unique scent releasing article. Other embodiments include unique methods, systems, devices, kits, assemblies, equipment, and/or apparatus related to scent releasing articles.

Further embodiments, forms, features, aspects, benefits, objects, and advantages of the present application shall become apparent from the detailed description and figures provided herewith.

BRIEF DESCRIPTION OF THE DRAWINGS

FIG. 1 is a plan view of a bracelet including a scent releasing article.

FIG. 2 is a section view of the scent releasing article illustrated in FIG. 1 taken along view line 2-2.

DETAILED DESCRIPTION OF REPRESENTATIVE EMBODIMENTS

Figure 3:
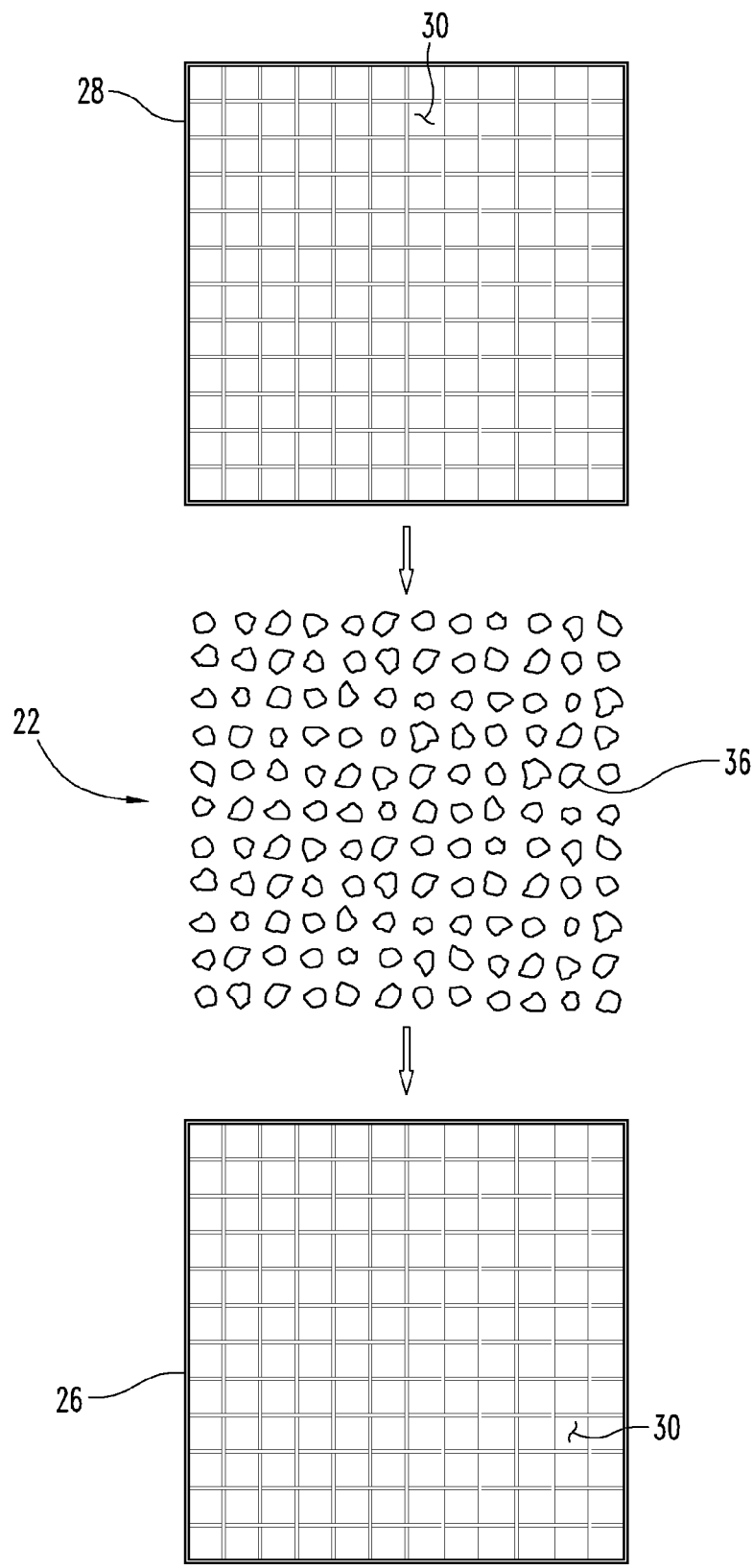
FIG. 3 is a schematic illustration of one technique for forming a composite structure of the scent releasing article illustrated in FIG. 1.

While the present application can take many different forms, for the purpose of promoting an understanding of the principles of the application, reference will now be made to the embodiments illustrated in the drawings and specific language will be used to describe the same. It will nevertheless be understood that no limitation of the scope of the application is thereby intended. Any alterations and further modifications of the described embodiments, and any further applications of the principles of the application as described herein are contemplated as would normally occur to one skilled in the art to which the application relates.

One embodiment of the present application is directed to a method that includes absorbing a first amount of fragrant oil with a polymer material and positioning the polymer material between opposing layers of mesh material each defining a plurality of interstitial openings to form a composite structure. The composite structure is then heated and pressed to fill at least a portion of the interstitial openings of the opposing layers of mesh material with a portion of the polymer material to produce a scent releasing article. In one form, the method further includes contacting the scent releasing article with a second amount of fragrant oil.

Referring now to FIG. 1, there is illustrated a bracelet 10 that includes one embodiment of a scent releasing article 12 according to the present application, although other forms are envisioned as will be discussed in greater detail below. Bracelet 10 includes opposite ends 14, 16 configured to releasably engage with one another to facilitate positioning of bracelet 10 around a wearer's wrist or ankle Scent releasing article 12 of bracelet 10 includes an elongate body 18 that extends between ends 14, 16 and is formed by a composite structure 20 which is illustrated in section view in FIG. 2. In the illustrated form, composite structure 20 of scent releasing article 12 generally extends between ends 14, 16 of bracelet 10. However, it should be appreciated that forms in which composite structure 20 of scent releasing article 12 forms only a portion of body 18 are also contemplated. For example, in one non-illustrated form, composite structure 20 can be positioned between opposite linking members coupled to ends 14, 16. In other non-illustrated forms, it is contemplated that body 18 may be formed of a material between ends 14, 16 that is distinct from composite structure 20 and to which composite structure 20 is coupled.

As illustrated in FIG. 2, composite structure 20 includes a polymer material 22 that contains a fragrant material, such as a fragrant oil, and is positioned between a first layer 24 of a mesh material or a loosely knitted structure and a second layer 28 of a mesh material or a loosely knitted structure. Further details regarding polymer material 22 and the fragrant material it contains will be provided below. In certain non-illustrated forms, it is contemplated that layers 24, 28 of the mesh material could also extend along one or both of sides 22a, 22b of polymer material 22 such that polymer material 22 is surrounded or circumscribed by the mesh material. In one particular form in which polymer material 22 is surrounded or circumscribed by the mesh material, the mesh material is formed as a bag or casing such that layers 24, 28 are coupled to one another. Each of layers 24, 28 of the mesh material defines a plurality of interstitial openings 26, 30, respectively, into which a portion of polymer material 22 extends. In one non-limiting form, the mesh material is formed from a cotton or polymer fabric and openings 26, 30 have sizes in the range of 0.1 to 10 millimeters, 0.5 to 5 millimeters, 0.8 to 3 millimeters, or 1 to 2 millimeters, although other values for the size of openings 26, 30 are possible and contemplated. In addition, it should be appreciated that other types of mesh materials may be used.

In the illustrated arrangement, polymer material 22 generally fills each of openings 26, 30 and extends flush with surfaces 24a, 28a of layers 24, 28, respectively, of the mesh material which generally face away from polymer material 22. It should be appreciated however that forms in which polymer 22 fills only a portion of openings 26, 30 and/or does not extend flush with one or both of surfaces 24a, 28a are also possible. In the illustrated arrangement, polymer material 22 generally becomes integrated with layers 24, 28 of the mesh material.

Composite structure 20 also includes a barrier member 32 which is positioned along surface 24a of layer 24 of the mesh material and extends along sides 22a, 22b of polymer material 22, although forms in which barrier member 32 does not extend along sides 22a, 22b of polymer material 22 are also possible. In addition, other non-illustrated forms where barrier member 32 extends along sides 22a, 22b and across a portion of surface 28a are also contemplated, and may be used to form, amongst other possibilities, bracelets, zipper-pulls and key chains. Forms in which barrier member 32 is omitted from composite structure 20 are also possible. While not previously discussed, it should be appreciated that barrier member 32 is generally configured to prevent the fragrant material contained in polymer 22 from coming into contact with the skin or clothing of a user of bracelet 10 and scent releasing article 12. In one non-limiting form, barrier member 32 includes a fabric material and a material impermeable to the fragrant material contained in polymer material 22 that is coupled to the fabric material and positioned between the fabric material and polymer material 22. Non-limiting examples of materials impermeable to the fragrant material contained in polymer material 22 that could be used in or for barrier member 32 include vinyl, polyvinyl chloride, polyethylene and polytetrafluoroethylene, just to provide a few possibilities. In one non-illustrated form, it also contemplated that layer 24 of the mesh material is absent such that barrier member 32 is positioned in direct contact with polymer material 22. In another form, it is also possible for barrier member 32 to include a mesh material that is bonded or adhered to the material impermeable to the fragrant material and used in lieu of layer 24 of the mesh material.

An optional cover layer 34 may be positioned over layer 28 of the mesh material to provide a decorative appearance to composite structure 20 if desired. However, if present, it should be appreciated that cover layer 34 will generally be air permeable to permit a scent or aroma to be released from scent releasing article 12.

Referring now to FIGS. 2 and 3 collectively, one non-limiting technique for producing scent releasing article 12 formed of composite structure 20 will now be described. More specifically, in one form, polymer material 22 is a thermoplastic, superabsorbent polymer material, non-limiting examples of which include sodium polyacrylate, potassium polyacrylate, lithium polyacrylate, and ammonium polyacrylate. In one aspect of this form, polymer material 22 is initially provided in a number of particles or granules 36, although forms in which polymer material 22 is provided in a solid or semi-solid sheet or other configuration are also possible. Particles 36 of polymer material 22 are soaked in the fragrant material until polymer material 22 is generally dry to the touch, although forms in which polymer material 22 is soaked in the fragrant material after formation of composite structure 20 are also possible. In one form, the fragrant material is a fragrant oil or oil-based fragrance, non-limiting examples of which include plant derived essential oils and synthetic fragrant oils.

Following absorption of the fragrant material by polymer material 22 (if performed before formation of composite structure 20), polymer material 22 is placed between layers 24, 28 of the mesh material and polymer material 22 and layers 24, 28 are then heated to a temperature of about 350 degrees Fahrenheit for about 5-10 minutes, although it should be appreciated that alternative values for the temperature and duration of heating are possible and contemplated. During heating, particles 36 of polymer material 22 soften and begin to extend into and fill openings 26, 30 of layers 24, 28 of the mesh material. In addition, after heating and before polymer material 22 and layers 24, 28 have cooled, polymer material 22 and layers 24, 28 of the mesh material are laid flat and rolled or pressed in order to further fill openings 26, 30 of the mesh material with polymer material 22. In addition, as particles 36 are heated, the outer surfaces thereof become softened or tacky such that upon pressing or rolling particles 36 may contact and adhere to one another. Thereafter, when polymer material 22 cools, the points of contact may become points of adhesion, although the same will still generally allow flexibility of polymer material 22 after it has cooled. The resulting composite structure 20 is adaptable for use in many applications. Moreover, when polymer material 22 is initially provided in a solid or semi-solid form, it may be heated to at least initiate filling of openings 26, 30 and then rolled or pressed as described above in order to continue filling openings 26, 30 with polymer material 22. In this form, it is also contemplated that polymer material 22 retains flexibility after its integration with layers 24, 28 such that composite structure 20 provides scent releasing article 12 with adaptability for use in many different applications. Further, it should be appreciated that the thickness of scent releasing article 12 may be varied depending on its intended use. By way of non-limiting example, in the illustrated form in which bracelet 10 includes scent releasing article 12, it may have a thickness in the range of about 3 millimeters to about 15 millimeters, although it should be understood that other variations are possible.

Following formation of composite structure 20, additional amounts of the fragrant material for absorption by polymer material 22 may then optionally be placed into contact with polymer material 22 and layers 24, 28 of the mesh material, although forms in which layers 24, 28 of the mesh material also absorb the fragrant material are possible. In other forms where composite structure 20 is formed before polymer material 22 absorbs any of the fragrant material, composite structure 20 can undergo one or more soakings in the fragrant material after formation for absorption of the fragrant material by polymer material 22 and, optionally, layers 24, 28 of the mesh material. While not previously discussed, it should be appreciated that the configuration of composite structure 20 will generally allow the portions of polymer material 22 which are positioned in openings 26, 30 to be in contact with the surrounding air such that a scent or aroma can be gradually released from composite structure 20. In one form, it is contemplated that composite structure 20 will be effective for releasing a desired scent or aroma for a period of one to six months, although different periods of time are also contemplated. It is also contemplated that composite structure 20 will release the desired scent or aroma for this period of time without requiring any additional heating or melting. While not intending to be bound by any single theory, it is believed that the above mentioned periods of time for release of the desired scent or aroma are accomplished by a relatively slow dissipation of the fragrant material from polymer material 22. In addition, these periods of time for release of the desired scent or aroma are also aided by the ability of polymer material 22 to generally prevent displacement of the fragrant material therefrom when it comes into contact with water. An article including composite structure 20 can be washed or otherwise cleaned without having a significant deleterious effect on the fragrant material contained therein. Further, it is contemplated that once scent releasing article 12 is no longer effective to provide the desired scent or aroma, it may be reloaded by additional soaking or other contact with the fragrant material in order to achieve continued release of the desired scent or aroma.

While not discussed above, it should be understood that in one form, after scent releasing article 12 including composite material 20 has been formed as described above, it can be cut or otherwise manipulated to provide a shape desired for its end use. Alternatively, it is also contemplated that composite structure 20 can be shaped or formed during the heating and pressing steps described above in order to provide scent releasing article 12 with a shape or configuration desired for its end use. It should be appreciated that scent releasing article 12 formed by composite structure 20 and including the fragrant material can be used for many purposes in addition to bracelet 10 illustrated in FIG. 1. For example, in certain embodiments scent releasing article 12 can be used to form or be attached to articles of clothing. In one non-limiting form of this embodiment, scent releasing article 12 can release an insect repelling scent and be attached to a shirt, pants, hat, sock, or other item to repel insects. In another form, scent releasing article 12 can release a scent calming to healthcare patients and be attached to clothing of a healthcare professional or an item intended to be worn by the patient, such as a bib or gown. In further embodiments, scent releasing article 12 may also be used to form other fashion accessories in addition to or in lieu of bracelet 10, non-limiting examples of which include anklets, necklaces, hair bands, hair clips, rings, earrings, sashes, scarves, key chains, zipper-pulls and pins amongst other possibilities. In one or more forms of these embodiments, these items can be formed in whole or in part from or include scent releasing article 12 which is capable of releasing a scent that is energizing, calming, therapeutic, attracting, sinus clearing, insect repelling, and/or appetite reducing, just to provide a few non-limiting examples. In still further embodiments, it is contemplated that scent releasing article 12 may also be attached to, used in, or form one or more paper or novelty products from which the emittance of a scent or aroma from composite structure 20 is desired. Non-limiting forms of these embodiments include greeting cards, magazines or restaurant menus to which scent releasing article 12 has been attached or coupled.

In one embodiment, a method includes absorbing a first amount of fragrant oil with a polymer material; positioning the polymer material between opposing layers of mesh material each defining a plurality of interstitial openings to form a composite structure; heating the composite structure; pressing the composite structure to fill at least a portion of the interstitial openings of the opposing layers of mesh material with a portion of the polymer material to produce a scent releasing article. In one form, the method further includes contacting the scent releasing article with a second amount of fragrant oil. In another form of this embodiment, the method further includes absorbing at least a portion of the second amount of fragrant oil with the polymer material. In yet another form, the polymer material is a superabsorbent polymer. In still another form, the polymer material is a thermoplastic polymer. In yet another form, the method also includes positioning an oil impermeable barrier member adjacent to one of the layers of mesh material. In one aspect of this form, the barrier member includes a vinyl-backed fabric. In another form of this embodiment, the scent releasing article is configured to release a scent from the fragrant oil from about one to about six months and in the absence of any additional heating or melting of the scent releasing article. In a further form, the method further includes forming at least a portion of at least one of an article of clothing and a fashion accessory from the scent releasing article. In one aspect of this form, the fashion accessory is at least one of a bracelet, anklet, earring, necklace, ring, key chain and zipper-pull. In another form, the method further includes positioning the scent releasing article in at least one of a greeting card and a menu.

In another embodiment, an article includes a polymer material positioned between opposing layers of mesh material and extending into interstitial openings of each of the layers of mesh material. The polymer material contains a fragrant oil from which an aroma may be released over time. In one aspect, the polymer material is a superabsorbent polymer. In another aspect, the polymer material is a thermoplastic polymer. In still another aspect, the article further includes an oil impermeable barrier member positioned adjacent to one of the layers of mesh material. In another aspect, the barrier member includes a cotton fabric backed with a vinyl material. In yet another aspect, the article further includes one or more components configured to facilitate wear by a user.

In yet another embodiment, a scent releasing article includes a thermoplastic superabsorbent polymer material containing a fragrant oil, and a mesh material defining a plurality of interstitial openings, and portions of the polymer material extend into the plurality of interstitial openings. In one form of this embodiment, the article further includes an oil impermeable barrier member positioned adjacent to the mesh material.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the application, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary. While the application has been illustrated and described in detail in the drawings and foregoing description, the same is to be considered as illustrative and not restrictive in character, it being understood that only the selected embodiments have been shown and described and that all changes, modifications and equivalents that come within the spirit of the application as defined herein or by any of the following claims are desired to be protected.

What is claimed is:

1. A method for producing a scent releasing article, comprising:
    absorbing a first amount of fragrant oil with a polymer material;
    positioning the polymer material between opposing layers of a mesh material each defining a plurality of interstitial openings to form a composite structure;
    heating the composite structure; and
    pressing the composite structure to fill at least a portion of the interstitial openings of each of the opposing layers of mesh material with a portion of the polymer material to produce the scent releasing article.

2. The method of claim 1, which further includes contacting the scent releasing article with a second amount of fragrant oil.

3. The method of claim 2, which further includes absorbing at least a portion of the second amount of fragrant oil with the polymer material.

4. The method of claim 1, wherein the polymer material is a superabsorbent polymer.

5. The method of claim 1, wherein the polymer material is a thermoplastic polymer.

6. The method of claim 1, which further includes positioning an oil impermeable barrier member adjacent to one of the layers of mesh material.

7. The method of claim 6, wherein the barrier member includes a vinyl-backed fabric.

8. The method of claim 1, wherein the scent releasing article is configured to release a scent from the fragrant oil for a period of time of about one to about six months.

9. The method of claim 1, which further includes forming at least a portion of at least one of an article of clothing and a fashion accessory with the scent releasing article.

10. The method of claim 9, wherein the fashion accessory is at least one of a bracelet, anklet, earring, necklace ring, key chain and zipper-pull.

11. The method of claim 1, which further includes positioning the scent releasing article in at least one of a greeting card, magazine and a menu.

12. A method for producing a scent releasing article, comprising:
    absorbing an amount of fragrant oil with a polymer material;
    positioning the polymer material between opposing layers of a mesh material each defining a plurality of interstitial openings to form a composite structure;
    heating the composite structure;
    pressing the composite structure to fill at least a portion of the interstitial openings of each of the opposing layers of mesh material with a portion of the polymer material; and
    producing the scent releasing article by way of the pressing, for releasing a scent of the fragrant oil, and such that the article has a front surface and a back surface each formed at least in part of the mesh material.

13. The method of claim 12 further comprising positioning an oil impermeable barrier member adjacent to one of the layers of mesh material.

* * * * *